(12) United States Patent
Duke et al.

(10) Patent No.: US 9,216,206 B2
(45) Date of Patent: Dec. 22, 2015

(54) METHODS OF TREATING SYMPTOMS ASSOCIATED WITH MENOPAUSE AND HORMONAL VARIATIONS WITH G-CSF

(75) Inventors: Debra M. Duke, Denver, CO (US); Richard C. Duke, Denver, CO (US)

(73) Assignee: MenoGeniX, Inc., Aurora, CO (US)

( * ) Notice: Subject to any disclaimer, the term of this patent is extended or adjusted under 35 U.S.C. 154(b) by 940 days.

(21) Appl. No.: 13/055,368

(22) PCT Filed: Jul. 22, 2009

(86) PCT No.: PCT/US2009/051429
§ 371 (c)(1),
(2), (4) Date: Sep. 28, 2011

(87) PCT Pub. No.: WO2010/011767
PCT Pub. Date: Jan. 28, 2010

(65) Prior Publication Data
US 2012/0014910 A1    Jan. 19, 2012

Related U.S. Application Data

(60) Provisional application No. 61/082,761, filed on Jul. 22, 2008.

(51) Int. Cl.
*A61K 38/19* (2006.01)
(52) U.S. Cl.
CPC .................... *A61K 38/193* (2013.01)
(58) Field of Classification Search
None
See application file for complete search history.

(56) References Cited

U.S. PATENT DOCUMENTS

| | | | |
|---|---|---|---|
| 5,399,345 A | 3/1995 | Schumacher et al. | |
| 5,416,195 A | 5/1995 | Camble et al. | |
| 5,534,526 A | 7/1996 | Cullinan | |
| 5,874,084 A | 2/1999 | Yng-Wong | |
| 5,981,551 A | 11/1999 | Luengo et al. | |
| 6,166,183 A | 12/2000 | Ishikawa et al. | |
| 6,245,812 B1 | 6/2001 | Gollobin | |
| 6,261,550 B1 | 7/2001 | Osslund | |
| 6,310,098 B1 | 10/2001 | Guttuso, Jr. | |
| 6,703,367 B1 | 3/2004 | Garnick | |
| 7,470,662 B2 | 12/2008 | Carter | |

FOREIGN PATENT DOCUMENTS

| | | |
|---|---|---|
| WO | WO-2005/039505 A2 | 5/2005 |
| WO | WO-2005/039505 A3 | 5/2005 |
| WO | WO-2005/051359 A1 | 6/2005 |
| WO | WO-2007/081293 A2 | 7/2007 |
| WO | WO-2007/081293 A3 | 7/2007 |
| WO | WO-2007/112581 A1 | 10/2007 |

OTHER PUBLICATIONS

Banfi et al., Cancer, 2001; 92: 2419-2428.*
Green et al., Annals of Oncology 2003; 14: 29-35.*
Chen et al., Journal of Steroid Biochemistry & Molecular Biology 83, 2003: 93-99.*
Phyllis Wise, "New Understanding of the Complexity of the Menopause and Challenges for the Future" in Biology of Menopause, Francis Bellino, Editor; Serono Symposia USA, 2000 Springer-Verlag New York, Inc.; pp. 1-8.*
Lewis, downloaded May 17, 2014 from permanent.access.gpo.gov/Ips1609/www.fda.gov/fdac/features/2000/300_arth.html.; a reprint of the article that originally appeared in the May-Jun. 2000 FDA Consumer, revised in Aug. 2000 and 2001; 9 pages total.*
Ollier et al., Best Practice & Research Clinical Rheumatology, 2001; 15: 27-48.*
Silman & Newman, Ann. Rheum. Dis., 1996; 55: 671-673.*
Yasui et al., Maturitas, 2007; 56: 396-403.*
Ushiroyama et al., The Journal of Alternative and Complementary Medicine, 10; 2004: 397-399.*
International Search Report mailed on Apr. 28, 2011 for PCT Application No. PCT/US2009/051429, filed on Jul. 22, 2009, 7 pages.
Mashiba, T. (2007). *The Bone* 21(5):87-91. (with English translation).
Miyajima, T. (2005). "Relationship of Osteoporosis and Osteoarthritis" *Rigakuryoho Kagaku* 20(3):241-244. (English abstract only).
Oda, T. et al. (2005). "Ovariectomy Fails to Augment Bone Resorption and Marrow B Lymphopoiesis in Granulocyte Colony-Stimulating Factor Transgenic Mice," *J Orthop Sci* 10(1):70-76.
Sato, O. et al. (2003). "3-H-10: Inhibition of the Marrow B-Cells Development Suppression by G-CSF, and After Ovariectomyosteoporosis," *Journal of the Japanese Society of Pathology* 92(1):224. (with English translation of 3-H-10).
Written Opinion mailed on Apr. 28, 2011 for PCT Application No. PCT/US2009/051429, filed on Jul. 22, 2009, 8 pages.
Office on Women's Health, U.S. Department of Health and Human Services (2014). "Menopause Basics," located at <http://www.womenshealth.gov/menopause/menopause-basics>, last visited Sep. 19, 2014, 6 pages.
Kollet, O. et al. (Oct. 7, 2007). "The Multiple Roles of Osteoclasts in Host Defense: Bone Remodeling and Hematopoietic Stem Cell Mobilization," *Annu. Rev. Immunol.* 25:51-69.
Takahashi, T. et al. (Apr. 1996). "Overexpression of the Granulocyte Colony-Stimulating Factor Gene Leads to Osteoporosis in Mice," *Lab. Invest.* 74(4):827-834.
Takamatsu, Y. et al. (Nov. 1, 1998). "Osteoclast-Mediated Bone Resorption is Stimulated During Short-Term Administration of Granulocyte Colony-Stimulating Factor But is Not Responsible for Hematopoietic Progenitor Cell Mobilization," *Blood* 92(9):3465-3473.

(Continued)

*Primary Examiner* — Christina Borgeest
(74) *Attorney, Agent, or Firm* — Morrison & Foerster LLP

(57) ABSTRACT

The invention provides for compositions and methods of treating or ameliorating menopausal symptoms and/or symptoms associated with hormonal variations by administering granulocyte colony-stimulating factor (G-CSF). The invention also provides for compositions and methods of treating or ameliorating arthritis using G-CSF.

20 Claims, No Drawings

(56) References Cited

OTHER PUBLICATIONS

Weilbaecher, K. N. (2000). "Mechanisms of Osteoporosis After Hematopoietic Cell Transplantation," *American Society for Blood and Marrow Transplantation* 165-174.

Yakisan, E. et al. (Oct. 1997). "High Incidence of Significant Bone Loss in Patients with Severe Congenital Neutropenia (Kostmann's Syndrome)," *the Journal of Pediatrics* 31(4):592-597.

Bartke, A. (2008). "Growth hormone and aging: A challenging controversy", *Clinical Interventions in Aging*, 3(4):659-665.

Carlo-Stella, C. et al. (May 1, 2004, e-published Jan. 15, 2004). "Use of Recombinant Human Growth Hormone (rhGH) Plus Recombinant Human Granulocyte Colony-Stimulating Factor (rhG-CSF) for the Mobilization and Collection of CD34+ Cells in Poor Mobilizers," *Blood* 103(9):3287-3295.

Chipman, J.J. et al. (Apr. 1997). "The Safety Profile of Gh Replacement Therapy in Adults," *Clin. Endocrinol. (Oxf)*. 46(4):473-481.

Fanciulli, G. et al. (May-Jun. 2009, e-published Feb. 18, 2009). "Growth Hormone, Menopause and Ageing: No Definite Evidence for 'Rejuvenation' with Growth Hormone," *Hum. Reprod. Update* 15(3):341-358.

Franco, C. et al (Mar. 2005, e-published Dec. 14, 2004). "Growth Hormone Treatment Reduces Abdominal Visceral Fat in Postmenopausal Women with Abdominal Obesity: a 12-Month Placebo-Controlled Trial," *J Clin Endocrinol Metab* 90(3):1466-1474.

Friedlander, A.L. et al. (Apr. 2001). "One Year of Insulin-Like Growth Factor I Treatment Does Not Affect Bone Density, Body Composition, or Psychological Measures in Postmenopausal Women," *J. Clin. Endocrinol. Metab.* 86(4):1496-1503.

Guiahi, M. et al. (Mar. 2015). "Can Human Recombinant Granulocyte-Colony Stimulating Factor Improve Menopausal Hot Flashes?: Results from a Pilot Study," Abstract LB-022, *presented at the Society for Reproductive Investigation 62nd Annual Scientific Meeting* Mar. 25-28, 2015, Late Breaking Abstracts, 3 pages.

Humatrope, Highlights of Prescribing Information (2014, revised Jul. 30, 2014), Eli Lily and Company, 19 pages.

Kehely, A. et al. (May 2002). "Short-Term Safety and Efficacy of Human GH Replacement Therapy in 595 Adults with GH Deficiency: a Comparison of Two Dosage Algorithms," *J. Clin. Endocrinol. Metab.* 87(5):1974-1979.

Melmed, S. et al. (Mar. 1987). "Acromegaly Update—Etiology, Diagnosis and Management," *West. J. Med.* 146(3):328-336.

Rudman, D. et al. (Jul. 5, 1990). "Effects of Human Growth Hormone in Men Over 60 Years Old", *The New England Journal of Medicine*, 323:1-6.

Taaffe, D.R. et al. (Mar. 2001). "Recombinant Human Growth Hormone, but Not Insulin-Like Growth Factor-I, Enhances Central Fat Loss in Postmenopausal Women Undergoing a Diet and Exercise Program," *Horm. Metab. Res.* 33(3):156-162.

Vance, M.L. (Jul. 5, 1990). "Growth Hormone for the Elderly?" *The New England Journal of Medicine*, 323:52-54.

Vance, M.L. (Feb. 27, 2003). "Can Growth Hormone Prevent Aging?," *The New England Journal of Medicine* 348(9):779-780.

Zamiri, C. et al. (May 2005). "Stabilization of Somatropin by Heparin," *J. Pharm. Pharmacol.* 57(5):555-564.

Boneberg, E. et al. (Sep. 26-29, 1999). Abstracts of the 39th Interscience Conference on Antimicrobial Agents and Chemotherapy, Abstract No. 1604, p. 386.

Fohlman, J. et al. (Sep. 1994). "Successful Treatment of Chronic Wound Infection in Neutropenia and Rheumatoid Arthritis with Filgrastim (rhG-GSF)," Annals of Hematology 69(3):153-156.

Graham, K.E. et al. (Jan. 1995). "A Prolonged Use of Granulocyte Colony Stimulating Factor in Felty's Syndrome," *Journal of Rheumatology* 22(1):174-176.

Guttuso, T. et al. (Feb. 2003). "Gabapentin's Effects on Hot Flashes in Postmenopausal Women: A Randomized Controlled Trial," *Obstet Gynecol* 101(2):337-345.

Lawlor, K.E. et al. (Aug. 3, 2004). "Critical Role for Granulocyte Colony-Stimulating Factor in Inflammatory Arthritis," *PNAS* 101(31)11398-11403.

McMullin, M.F. et al. (Mar. 1995). "Felty's Syndrome Treated with rhG-CSF Associated with Flare of Arthritis and Skin Rash," *Clinical Rheumatology* 14(2):204-208.

Morris, G.L. (1999). "Gabapentin," *Epilepsia* 40(Suppl. 5):S63-S70.

Nelson, H.D. et al. (May 3, 2006). "Nonhormonal Therapies for Menopausal Hot Flashes," *JAMA* 295(17) 2057-2071.

Souza, L.M. et al. (Apr. 4, 1986). "Recombinant Human Granulocyte Colony-Stimulating Factor: Effects on Normal and Leukemic Myeloid Cells," *Science* 232:61-65.

Ushiroyama, T. et al. (Apr. 2004). "A Pilot Study of a Kampo Formula, EH0202, with Intriguing Results for Menopausal Symptoms," *Journal of Alternative and Complementary Medicine* 10(2):397-399.

Yasui, T. et al. (Apr. 20, 2007, e-published Dec. 11, 2006). "Changes in Serum Cytokine Concentrations During the Menopausal Transition," *Maturitas* 56(4):396-403.

\* cited by examiner

METHODS OF TREATING SYMPTOMS ASSOCIATED WITH MENOPAUSE AND HORMONAL VARIATIONS WITH G-CSF

CROSS REFERENCE TO RELATED APPLICATIONS

This application is a national stage application of International Patent Application No. PCT/US2009/051429, filed on Jul. 22, 2009, which claims the benefit of priority to U.S. Provisional Application No. 61/082,761, filed on Jul. 22, 2008, the disclosures of which are herein incorporated by reference in their entirety.

TECHNICAL FIELD

This invention relates to compositions and methods of treating or ameliorating menopausal symptoms and/or symptoms associated with hormonal variations by administering granulocyte colony-stimulating factor (G-CSF). The invention also provides compositions and methods of treating or ameliorating arthritis using G-CSF.

BACKGROUND OF THE INVENTION

Menopausal syndrome is related to endocrine, somatic, and psychological changes that occur as the hormonal balance in the female body changes and the menstrual cycle ceases due to the senescence of the ovaries. Menopausal syndrome includes a number of varying and often highly distressing symptoms such as hot flashes, headaches, joint pain, myalgia and general malaise. In particular, hot flashes are a frequent symptom, experienced by more than 50% of menopausal women, and can persist for several years after menopause. For some women, menopausal symptoms are mild and manageable by making life-style changes, including more exercise, dietary changes and stress management, or by using alternative therapies such as acupuncture, massage or chiropractic therapy. For many others, however, symptoms are much more severe and interfere substantially with daily activities or sleep, requiring more potent treatment.

The main treatment to date for menopausal symptoms is the use of hormone-therapy such as estrogen alone, estrogens combined with progesterone, or phytoestrogens. However, the use of estrogens is associated with potentially significant health risks including blood clots, cardiovascular disease, stroke and slight increase in risk of breast cancer when estrogen is taken together with progesterone. Due to concerns about these adverse effects and the fact that hormone-therapy is contraindicated in women with breast cancer, interest in alternative medications to treat menopausal symptoms has been increasing.

Various known, non-hormonal agents have been tested for their efficacy in treating menopausal symptoms (Nelson et al., *JAMA* 295 (17): 2057-71 (2008)). Among these, antidepressants from classes of medications known as selective serotonin reuptake inhibitors (SSRIs) and serotonin and norepinephrine reuptake inhibitors (SNRIs), including venlafaxine (Effexor), paroxetine (Paxil), fluoxetine (Prozac), citalopram (Celexa) and others, have been found to relieve hot flashes in some clinical trials. However, they are not as efficient as hormone-therapy and adverse effects such as nausea and insomnia have been reported. Compounds that bind to the $\alpha_2\delta$ subunit of a voltage gated calcium channel such as gabapentin have also been described as treatment for hot flashes, nausea, emesia and fever (see, e.g., U.S. Pat. No. 6,310,098). Gabapentin is approved as an anti-epileptic agent, and has also been used in the treatment of neurogenic pain, restless legs syndrome, essential tremor, bipolar disorder and migraine (Morris GL, *Epilepsia* 40:S63-S70 (1999)). Gabapentin was only moderately effective in treating hot flashes compared to hormone-therapy and side-effects including somnolence, dizziness and peripheral edema were common (Guttuso et al., *Obstet Gynecol*, 101:337-345 (2003)). Contradictory results have been reported for clonidine, an a-adrenergic agonist, which reduced hot flashes in some trials, but showed no effect in others. Even though these drugs appeared to have some efficacy against hot flashes, they were not as potent as hormone-therapy and all caused substantial adverse effects. Additional therapies to reduce hot flashes have been proposed including traditional Chinese medicine (WO 2007/081293), leucine (U.S. Pat. No. 6,245,812), ingestible material comprising a herbal complex (U.S. Pat. No. 5,874,084), and luteinizing-hormone-releasing hormone antagonists, (U.S. Pat. No. 6,703,367). However, to date their efficacy and safety has not been thoroughly assessed.

Menopausal symptoms other than hot flashes such as osteoporosis and raised total and LDL cholesterol levels can be treated by selective estrogen-receptor modulators (SERMS), such as raloxifene (U.S. Pat. No. 5,534,526), which selectively bind to and activate the estrogen receptors of some tissues such as bone and block the receptors of others, e.g., breast and uterus. Although raloxifene (Evista) was found to be beneficial for some menopausal symptoms, it does not reduce hot flashes and is associated with serious side effects such as venous thrombembolic events.

Accordingly, there is a need to identify an effective and safe treatment for menopausal symptoms, since current medications are often associated with negative side-effects or fail to show consistent positive results. The invention described herein fulfills this need and provides additional benefits as well.

Arthritis is a group of conditions involving acute or chronic inflammation of a joint, resulting from infection, trauma, degenerative changes, metabolic disturbances, autoimmune disease or other causes. It occurs in various forms, such as osteoarthritis, gout and pseudogout arthritis, ankylosing spondilitis, psoriatic arthritis, systemic lupus erythematosus, septic arthritis or rheumatoid arthritis. Common symptoms of arthritis include swelling, stiffness and constant or recurring pain in one or more joints. In some patients with certain forms of arthritis, symptoms can also include fever, gland swelling, weight loss, fatigue, feeling unwell, and even symptoms from abnormalities of organs such as the lungs, heart, or kidneys.

The most common type of arthritis is osteoarthritis. This type of arthritis affects an estimated 21 million adults in the United States. Osteoarthritis primarily affects cartilage, which is the tissue that cushions the ends of bones within the joint. In osteoarthritis, the cartilage begins to fray and may entirely wear away. Osteoarthritis can cause joint pain and stiffness. Disability results most often when the disease affects the spine and the weight-bearing joints (the knees and hips). Apart from heat application, weight control and appropriate exercise and rest, as well as dietary supplements, additional medications to reduce pain and inflammation in patients suffering from osteoarthiritis include acetaminophen, non-steroidal anti-inflammatory drugs (diclofenac, ibuprofen, napoxen or COX-2 selective inhibitors), cortocosteroids (nowadays avoided), and narcotics for severe pain.

The many forms of arthritis make up the most common chronic illness in the United States. For some types of arthritis, the underlying cause has not yet been identified and therefore only symptomatic treatments are being developed. Current treatments include a wide variety of medications due to the variability in symptoms, many of which are associated with risks and are beneficial only in certain groups of patients. Accordingly, there is a need to find medications with high efficacy for various arthritic symptoms and low risks and side-effects. The invention described herein fulfills this need and provides additional benefits as well.

All references cited herein, including, without limitation, patents, patent applications and scientific references, are hereby incorporated in their entirety.

SUMMARY OF THE INVENTION

The invention provides for compositions and methods of treating and/or ameliorating the symptoms associated with menopause, hormonal variations, and arthritis. Accordingly, in one aspect, the invention provides a method of treating, ameliorating, alleviating or preventing symptoms associated with menopause or reducing their frequency in an individual in need thereof by administering an effective amount of G-CSF. In another aspect, the invention is directed to methods of treating, ameliorating, alleviating or preventing symptoms associated with hormonal variations or reducing the frequency of these symptoms in an individual in need thereof by administering an effective amount of G-CSF. The invention further encompasses a method of alleviating discomfort or palliating pain associated with menopausal symptoms or with symptoms caused by hormonal variations in an individual in need thereof by administering an effective amount of G-CSF.

The individual in any of the methods above can be any mammalian individual, preferable a human individual. In certain embodiments the individual in need thereof is a female undergoing menopause. In other embodiments the individual in need thereof is a postmenopausal female. In yet other embodiments, the individual in need thereof is a female experiencing hormonal variation. In further embodiments, the individual in need thereof is a male experiencing hormonal variation. Menopause or hormonal variations in these individuals can occur naturally or they can be drug-induced or surgically-induced. In one aspect, the treatment reduces the frequency of hot flashes in an individual in need thereof such treatment.

In a further aspect, the invention provides a method of treating, ameliorating, alleviating or preventing arthritis in an individual in need thereof by administering an effective amount of G-CSF. The invention also contemplates a method of treating, ameliorating, alleviating or preventing symptoms associated with arthritis in an individual in need thereof by administering an effective amount of G-CSF. The invention is further directed to a method of alleviating discomfort or palliating pain associated with arthritis. In one embodiment, the invention provides a method of treating, ameliorating, alleviating or preventing osteoarthritis in an individual in need thereof by administering an effective amount of G-CSF. In another preferred embodiment, the invention is directed to a method of treating, ameliorating, alleviating or preventing joint pain in an individual in need thereof by administering an effective amount of G-CSF. The invention further provides for methods wherein treatment ameliorates one or more symptoms associated with arthritis wherein the symptoms are selected from the group consisting of joint pain, limited function of joints, joint stiffness, swelling, redness and warmth. The invention further provides for methods wherein treatment ameliorates one or more symptoms associated with arthritis wherein the symptoms are selected from the group consisting of fever, gland swelling, weight loss and fatigue.

The individual can be any mammalian individual, preferable a human individual. In one aspect, the individual in need thereof is a female. In another aspect, the individual in need thereof is a male. In some aspects, the individual in need thereof is a female undergoing menopause and/or suffering from osteoarthritis. In other aspects, the individual in need thereof is a postmenopausal female or a female experiencing hormonal variation who is suffering from osteoarthritis. In further aspects, the individual in need thereof is a postmenopausal female or a female experiencing hormonal variation or a female who is suffering from osteoarthritis. In some aspects, the individual in need thereof is a male experiencing hormonal variation and/or suffering from osteoarthritis.

In any of the methods above, in one aspect, the G-CSF is administered at a dose of 5 mcg/kg bodyweight. In another aspect, G-CSF is administered at a dose of 5-10 mcg/kg bodyweight. In another aspect, G-CSF is administered at a dose of 2-10 mcg/kg bodyweight. In another aspect, G-CSF is administered at a dose of 2-20 mcg/kg bodyweight. In another aspect, G-CSF is administered once every about one to two months. In another aspect, G-CSF is administered once every about two to three months. In another aspect, G-CSF is administered once every about three to four months.

In any of the methods above, in one aspect, G-CSF is administered subcutaneously or intravenously. In some aspects, G-CSF is administered parenterally, enterically, topically or via inhalation. In other aspects, G-CSF is formulated in the commercially available composition filgrastim, pegfilgrastim or lenograstim. In another aspect, G-CSF is present in a pharmaceutical composition comprising G-CSF and a pharmaceutically-acceptable carrier.

DETAILED DESCRIPTION OF THE INVENTION

The present invention is based, in part, on the observation that granulocyte colony-stimulating factor (G-CSF) is capable of treating and/or ameliorating symptoms associated with menopause, hormonal variations, and/or arthritis.

General Techniques

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000); *Casarett and Dotes Toxicology The Basic Science of Poisons*, C. Klaassen, ed., 6th edition (2001), and *Vaccines*, S. Plotkin and W. Orenstein, eds., $3^{rd}$ edition (1999). Unless defined otherwise, technical and scientific terms used herein have the same meaning as commonly understood by one of ordinary skill in the art to which this invention belongs.

Definitions

For purposes of interpreting this specification, the following definitions will apply and whenever appropriate, terms used in the singular will also include the plural and vice versa.

In the event that any definition set forth below conflicts with any document incorporated herein by reference, the definition set forth below shall control.

As used herein, the term "menopausal symptoms" includes, but is not limited to, one or more of the following symptoms: hot flashes; night sweats; headache; migraines; dizziness; sleep disorders; fatigue; formication; nausea; emesis; palpitations; pain including but not limited to joint pain; loss of bone density (osteoporosis); myalgia; mood swings; forgetfulness; general malaise; changes in serum lipid levels; changes in urination; weight gain and shift; skin, hair and eye changes; dryness of the eyes, mouth, nose and vagina; pain with intercourse; and decreased libido.

As used herein, "treatment" refers to clinical intervention in an attempt to alter the natural course of the individual, and can be performed before or during the course of clinical pathology. Desirable effects of treatment include: alleviating the condition or symptoms associated with menopause, hormonal variations, or arthritis; diminishing any direct or indirect pathological consequences of the condition or symptoms associated with menopause, hormonal variations, or arthritis; decreasing the rate of progression; and ameliorating or palliating the discomfort and/or pain from symptoms associated with menopause, hormonal variations, or arthritis. In some embodiments, methods and compositions of the invention are useful in attempts to delay development of symptoms associated with menopause, hormonal variations, or arthritis. In other embodiments, methods and compositions of the invention are useful in attempts to delay development of menopause, hormonal variations, or arthritis.

"Receiving treatment" includes initial treatment and/or continuing treatment. As used herein, "treatment" is an approach for obtaining beneficial or desired results, preferably including clinical results. For purposes of this invention, beneficial or desired clinical results include, but are not limited to, one or more of the following: alleviation of one or more symptoms, diminishment of extent of the condition and/or disease, stabilized (i.e., not worsening) state of condition and/or disease, preventing spread of the condition and/or disease, preventing occurrence or recurrence of the symptoms associated with menopause, hormonal variations, or arthritis, amelioration of the disease state or symptoms associated with conditions described herein, remission (whether partial or total), reduction of incidence of disease and/or symptoms, stabilizing (i.e., not worsening) of the disease state or symptoms associated with conditions described herein.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular symptom, such as that associate with menopause, hormonal variations, or arthritis. A therapeutically effective amount herein may vary according to factors such as the disease state, age, sex, and weight of the patient. A therapeutically effective amount is also one in which any toxic or detrimental effects of G-CSF are outweighed by the therapeutically beneficial effects.

As used herein, a "medicament" is an active drug to treat symptoms of a clinical condition, such as menopause, hormonal variations, or arthritis. In one embodiment, the medicament is used to treat symptoms associated with menopause, hormonal variations, or arthritis. Such medicaments can be also considered a "therapeutic agent," and, as such "therapeutic agent effective to treat menopause, hormonal variations, or arthritis," and grammatical variations thereof, as used herein, refer to an agent that when provided in an effective amount is known, clinically shown, or expected by clinicians to provide a therapeutic benefit in an individual who has menopause, hormonal variations, or arthritis. In one embodiment, the phrase includes any agent that is marketed by a manufacturer, or otherwise used by licensed clinicians, as a clinically-accepted agent that when provided in an effective amount would be expected to provide a therapeutic effect in an individual who has menopause, hormonal variations, or arthritis.

An "individual" is a vertebrate, preferably a mammal, more preferably a human. Mammals include, but are not limited to farm animals, sport animals, pets, primates, mice and rats. "Individuals" would also include any animals used in animal models for experimental testing for various diseases (e.g., mouse model for arthritis).

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X."

Methods of the Invention

The invention provides for methods for treating and/or ameliorating symptoms associated with menopause, hormonal variation and/or arthritis in individuals in need thereof by administering an effective amount of granulocyte colony-stimulating factor (G-CSF) to the individual.

Granulocyte Colony-stimulating Factor (G-CSF)

Colony stimulating factors are glycoproteins, which act on hematopoietic cells by binding to specific cell surface receptors and stimulating proliferation, differentiation commitment and some end-cell functional activation. G-CSF is a lineage specific colony-stimulating factor, which is produced by monocytes, fibroblasts, and endothelial cells. It regulates production of neutrophils within the bone marrow, and affects neutrophil progenitor proliferation and differentiation. Furthermore, G-CSF can significantly increase the ability of neutrophils to kill tumor cells in vitro through antibody mediated cellular cytotoxicity (Souza et al., *Science* 232:61-65 (1986)).

G-CSF is commercially available under the names filgrastim (Neupogen®, Amgen and Granocyte®, Merck), pegfilgrastim (Neulasta®, Amgen) and lenograstim (Neutrogrin®, Chugai). Filgrastim is used to prevent infectious complications associated with neutropenia, a decrease in the number of neutrophils in the body. Neutropenia may develop in cancer patients receiving chemotherapy or undergoing bone marrow transplantation. Neutropenia also may occur for unknown reasons in adults and infants. Filgrastim is also used in healthy patients who will be donating bone marrow if their white blood cell counts are low.

In addition to its anti-infectious action via neutrophils, G-CSF/filgrastim has also been reported to cause anti-inflammatory immunomodulation via monocytes (Boneberg et al., *Interscience Conference on Antimicrobial Agents and Chemotherapy*, Sep 26-29; 39: 386; Abstract No. 1604 (1999). Healthy volunteers treated with G-CSF/filgrastim showed an attenuated release of TNF-a, IL-12, IL-1β and IFN-γ in response to G-CSF/filgrastim treatment, which enables it for use in neutropenic and non-neutropenic infections. Furthermore, G-CSF was shown to prevent spontaneous abortions or implantation failure during assisted reproduction and to enhance reproductive fitness (U.S. patent publication 2007/0071716). Notably, a recent study on the role of G-CSF in inflammatory joint disease revealed that G-CSF deficient mice were protected from chronic and acute arthritis, suggesting G-CSF as a target to treat inflammatory joint disease such as rheumatoid arthritis (Lawlor et al., PNAS, 101 (31): 11398-11403 (2004)).

Accordingly, in one aspect, the invention provides a method of treating, ameliorating, alleviating or preventing menopausal symptoms or reducing their frequency in individuals in need thereof by administering an effective amount of G-CSF to the individual. In a preferred aspect of the invention, the individual is a human individual. Common symptoms experienced by women undergoing menopause or by women post-menopause, and for which this invention provides treatment, include, but is not limited to, hot flashes; night sweats; headache; migraines; dizziness; sleep disorders; fatigue; formication; nausea; emesis; palpitations; pain including but not limited to joint pain; loss of bone density (osteoporosis); myalgia; mood swings; forgetfulness; general malaise; changes in serum lipid levels; changes in urination; weight gain and shift; skin, hair and eye changes; dryness of the eyes, mouth, nose and vagina; pain with intercourse; and decreased libido.

In particular, hot flashes are a very frequent symptom and have a strong impact on the daily life of many menopausal women. A hot flash, or flush, is characterized by a sudden feeling of warmth to intense heat spreading through the face and upper body. It is usually evidenced by a visible flushing of the skin and often associated with sweating, which can last from a few seconds up to a few minutes. Some women also experience rapid heartbeat (palpitations), nausea, dizziness, anxiety, or a feeling of weakness. The cause of hot flashes is poorly understood. According to the current theory, endorphin concentrations in the hypothalamus decrease with declining estrogen production, enhancing release of nor-epinephrine and serotonin, leading to an inappropriate heat-loss mechanism (Nelson et al., JAMA, 295 (17): 2057-71(2008)).

Menopausal symptoms can be caused by natural menopause in a female or by drug-induced or surgically-induced events. In certain cases, natural menopause can be premature and start as early as in the mid-30s. Surgically-induced menopause refers to menopause caused by bilateral oophorectomy (surgical removal of the ovaries) or by hysterectomy (surgical removal of the uterus) performed for various gynecological reasons. In case of hysterectomy, when one or both ovaries are conserved, they can continue producing hormones until the normal age of menopause or they may stop producing hormones sooner than expected. Furthermore, menopausal symptoms can be caused by drug-induced menopause. Drug-induced menopause refers to menopause in female patients receiving hormone-therapy for gynecological cancers (breast, cervical, ovarian or vaginal) or for any gynecological disease for which estrogen and progesterone secretion must be blocked to prevent disease progression. Drug-induced menopause can also occur when the ovaries are gravely damaged by radiation, chemotherapy or other medications.

The invention also encompasses methods of treating, alleviating, ameliorating or preventing symptoms associated with hormonal variation or reducing frequency of these symptoms in individuals in need thereof by administering an effective amount of G-CSF to the individual. Changes in hormonal levels also occur in individuals other than menopausal females and can cause a variety of symptoms similar to the menopausal symptoms described above. In a preferred aspect of the invention, the individual is a human individual. In another aspect, the individual is a female human experiencing hormonal variations. In another aspect, the individual is a male human experiencing hormonal variations.

Hormonal variation can be caused naturally or they can be induced by surgery or medication in females or males. For example, hormone levels in males receiving hormone deprivation therapy or who had orchiectomy have reduced testosterone levels. Typical symptoms associated with these treatments in males include, but are not limited to hot flashes, breast tenderness and growth of breast tissue, osteoporosis, anemia, decreased mental acuity, loss of muscle mass, weight gain, fatigue, decrease in HDL and depression.

The invention further provides a method of treating, alleviating, ameliorating or preventing arthritis or arthritic symptoms in individuals in need thereof by administering to the individual an effective amount of G-CSF. In a preferred aspect of the invention, the individual is a human individual. In another aspect, the individual is a female human experiencing arthritis or arthritic symptoms. In another aspect, the individual is a female human who is experiencing both arthritis or arthritic symptoms and menopausal symptoms. In another aspect, the individual is a male human experiencing arthritis or arthritic symptoms. In another aspect, the individual is a male human who is experiencing both arthritis or arthritic symptoms and hormonal variations.

Arthritis can occur in several forms including, but not limited to, osteoarthritis, gout arthritis, pseudogout arthritis, ankylosing spondilitis, psoriatic arthritis, systemic lupus erythematosus, and septic arthritis. The causes of arthritis depend on the form of arthritis and the various types differ largely in their characteristics, treatments and prognosis. They are similar in that they have a tendency to affect the joints, muscles, ligaments, cartilage, tendons, and many have the potential to affect internal body areas. Symptoms of arthritis include pain and limited function of joints. Inflammation of the joints in arthritis is characterized by joint stiffness, swelling, redness, and warmth. Tenderness in the inflamed joint can be present as well and in some cases snapping of the joints, bony growths at the joint or abnormal angulation of the joint is observed. Many of the forms of arthritis, because they are rheumatic diseases, can cause symptoms affecting various organs of the body that do not directly involve the joints. Therefore, symptoms in some patients with certain forms of arthritis can also include, but is not limited to, fever, gland swelling, weight loss, fatigue, feeling unwell, and symptoms from abnormalities of organs such as the lungs, heart or kidneys.

Osteoarthritis is the most common form of arthritis and is caused by abnormal wearing of the cartilage. Although osteoarthritis is typically present in older people, also people of younger age can be affected. While age is positively correlated with osteoarthritis, it merely illustrates that this disease takes time to develop and it is not clear what exactly leads to the breakdown of the cartilage. Although not intending to be bound by any theory, osteoarthritis often coincides with menopause and thus, the changes undergoing in the female body during this period may partly be responsible for the onset or worsening of osteoarthritis. As such, in one aspect, the methods of the present invention for treating osteoarthritis are applicable to females undergoing menopause and concomitantly suffering from osteoarthritis, as well as to postmenopausal females suffering from osteoarthritis, as well as to premenopausal females who developed osteoarthritis at a young age, for example as a result of an injury or cumulative trauma. In another aspect of the invention, male individuals who have arthritis, including osteoarthritis, may also be treated with G-CSF. In yet another aspect of the invention, male individuals who have both arthritis (including osteoarthritis) and hormonal variations may also be treated with G-CSF.

With respect to the individuals for whom the treatment is contemplated, it is understood that the individual is generally under care of a physician who can oversee the treatment plan to ensure efficacy and other safety aspects. The individual may be a patient of a physician for treatment for pain or discomfort associated with menopause, hormonal variations or arthritis. However, the invention also contemplates treatment for individuals who are not under the care of a physician for solely these indications (e.g., menopause, hormonal variations or arthritis).

Dose, Formulation and Administration

To practice methods of the invention, G-CSF is typically administered at an amount that is effective to achieve therapeutic benefits (e.g., a therapeutically effective amount), such as ameliorating the pain and/or discomfort associated with menopause, hormonal variations and arthritis. One of skill in the art, such as a clinician, can aid in determining an amount which is a therapeutically effective amount based on well-known parameters, such as weight of the individual and medical history.

In some aspects of the invention, a therapeutically effective amount of G-CSF for treating an individual in need thereof is about 5 mcg/kg (mcg=micrograms, kg=kilograms) bodyweight. In other aspects, the amount of G-CSF is increased to a dose of about 5-10 mcg/kg bodyweight. Since the amount necessary to achieve a therapeutic effect is dependent on the severity of the symptoms and diseases described herein, as well as on the individual, doses of G-CSF between about 2-10 mcg/kg bodyweight or between about 2-20 mcg/kg bodyweight can be administered and may be adjusted depending on the severity of the symptoms and/or disease state.

Typically, G-CSF is administered once every about one to two months to treat, ameliorate, prevent or reduce the frequency of the symptoms described herein. In less severe cases, G-CSF is administered once every about two to three months. In very mild cases, G-CSF is administered once every about three to four months. In one aspect, G-CSF is administered only once as a treatment. In other aspects, G-SCF is administered twice as a treatment. The frequency of administration is dependent on the severity of the symptoms described herein as well as on the individual suffering from these symptoms. As such, the dose and frequency of treatment may be adjusted as necessary as determined by a practitioner skilled in the art. For example, a physician may monitor one or more symptoms in a patient being treated with G-CSF according to this invention and, upon observing attenuation of one or more symptoms for a period of time, conclude that the patient can sustain the positive effects of the treatment described herein without further administration of G-CSF for a period of time. If necessary, the patient may return at a later point time for additional treatment as needed.

G-CSF can be administered by any mode of administration known to those of skill in the art. Preferably, G-CSF is administered subcutaneously or intravenously. Other methods of administration include, but are not limited to parenteral, enteral, topical administration or inhalation. Alternatively, transdermal delivery systems manufactured as adhesive disc or patch that slowly releases the active ingredient for percutaneous absorption can be used. Permeation enhancers can be added to these delivery systems to facilitate penetration of the G-CSF. Furthermore, devices which allow slow release of the active ingredient and are suitable for implantation can be applied for administration of G-CSF.

The G-CSF administered in the methods of the invention can be any G-CSF known to those of skill in the art without limitation. In certain embodiments, G-CSF is a commercially available G-CSF available as a pharmaceutical composition suitable for administration to an animal, including a human. Such commercially available compositions can be, but are not limited to, filgrastim (Neupogen®, Amgen and Granocyte®, Merck), pegfilgrastim (Neulasta®, Amgen) and lenograstim (Neutrogrin®, Chugai).

The invention further contemplates use of G-CSF derivatives, mimetics, variants, chemically modified compounds. See, e.g., U.S. Publication No. 2007/0071716 and U.S. Pat. Nos. 5,399,345; 5,416,195; 5,981,551; 6,166,183 and 6,261,550.

Kits of the Invention

The invention provides for kits comprising a therapeutically effective amount of G-CSF formulated for use in a human individual who is experiencing symptoms associated with menopause, hormonal variations or arthritis (e.g., osteoarthritis). Instruction sheets for use are optionally provided. The kit can include G-CSF in a therapeutic amount that is formulated for most effective delivery (e.g., subcutaneous, intravenous, parenteral, enteral, topical, inhalation, transdermal, etc.). The G-CSF can be packaged in a manner to allow for one time use or multiple uses.

The following examples are provided for illustrative purposes only and are not intended to limit the scope of the invention in any manner.

EXAMPLE

Example 1 G-CSF Alleviates Menopausal Symptoms

A female individual who was experiencing symptoms of menopause was given a single dose of 300 mcg (5 mcg/kg) filgrastim to boost production of neutrophil granulocytes. The female individual experienced a dramatic reduction of menopausal symptoms such as hot flashes, fatigue, sleep disorders, night sweats, joint pain, forgetfulness and mood swings within one week of administration of filgrastim, which lasted for 4 to 6 weeks.

Example 2 G-CSF Alleviates Symptoms Associated with Osteoarthritis

A female individual who was experiencing symptoms of menopausal symptoms and arthritic pain was given a single dose of 300 mcg (5 mcg/kg) filgrastim to boost production of neutrophil granulocytes. The female individual experienced a dramatic reduction of joint pain swelling and stiffness associated with osteoarthritis within one week of receiving filgrastim for 8 to 12 weeks.

What is claimed is:

1. A method of treating a symptom caused by naturally occurring or surgically-induced menopause in an individual in need thereof, comprising: administering to the individual an effective amount of granulocyte colony stimulating factor (G-CSF).

2. The method according to claim 1, wherein the treatment reduces the frequency of hot flashes.

3. The method according to claim 1, wherein G-CSF is administered at a dose of about 5 mcg/kg bodyweight.

4. The method according to claim 1, wherein G-CSF is administered at a dose of about 2-20 mcg/kg bodyweight.

5. The method according to claim 1, wherein G-CSF is administered once every about one to two months.

6. The method according to claim 1, wherein G-CSF is administered once every about two to three months.

7. The method according to claim 1, wherein G-CSF is administered once every about three to four months.

8. The method according to claim 1, wherein G-CSF is administered subcutaneously or intravenously.

9. The method according to claim 1, wherein G-CSF is administered parenterally, enterically, topically or via inhalation.

10. The method according to claim 1, wherein G-CSF is formulated in the commercially available composition Filgrastim, Pegfilgrastim or Lenograstim.

11. The method according to claim 1, wherein G-CSF is present in a pharmaceutical composition comprising G-CSF and a pharmaceutically-acceptable carrier.

12. The method of claim 1, wherein the individual is additionally suffering from osteoarthritis.

13. The method of claim 1 wherein the symptom comprises one or more of hot flashes; night sweats; headache; migraines; dizziness; sleep disorders; fatigue; formication; nausea; emesis; palpitations; pain including joint pain; loss of bone density (osteoporosis); myalgia; mood swings; forgetfulness; general malaise; changes in serum lipid levels; changes in urination; weight gain and shift; skin, hair and eye changes; dryness of the eyes, mouth, nose and vagina; pain with intercourse; and decreased libido.

14. The method of claim 1, wherein the symptom comprises one or more of hot flashes; fatigue; sleep disorders; night sweats; joint pain; forgetfulness; and mood swings.

15. The method of claim 1 wherein the individual is either undergoing menopause or is postmenopausal.

16. A method of alleviating discomfort or pain associated with a menopausal symptom caused by naturally occurring or surgically-induced menopause in an individual in need thereof comprising: administering to the individual an effective amount of granulocyte colony-stimulating factor (G-CSF).

17. The method of claim 16, wherein the pain is a joint pain.

18. The method of claim 16 wherein the symptom comprises one or more of hot flashes; night sweats; headache; migraines; dizziness; sleep disorders; fatigue; formication; nausea; emesis; palpitations; pain including joint pain; loss of bone density (osteoporosis); myalgia; mood swings; forgetfulness; general malaise; changes in serum lipid levels; changes in urination; weight gain and shift; skin, hair and eye changes; dryness of the eyes, mouth, nose and vagina; pain with intercourse; and decreased libido.

19. The method of claim 16, wherein the symptom comprises one or more of hot flashes; fatigue; sleep disorders; night sweats; joint pain; forgetfulness; and mood swings.

20. The method of claim 16 wherein the individual is either undergoing menopause or is postmenopausal.

* * * * *